US009775797B2

(12) United States Patent
Gadgil et al.

(10) Patent No.: US 9,775,797 B2
(45) Date of Patent: Oct. 3, 2017

(54) PERSONAL CARE COMPOSITION

(71) Applicant: Conopco, Inc., Englewood Cliffs, NJ (US)

(72) Inventors: Vijay Ramchandra Gadgil, Bangalore (IN); Praful Gulab Rao Lahorkar, Bangalore (IN)

(73) Assignee: Conopco, Inc., Englewood, NJ (US)

( * ) Notice: Subject to any disclaimer, the term of this patent is extended or adjusted under 35 U.S.C. 154(b) by 403 days.

(21) Appl. No.: 14/386,872

(22) PCT Filed: Mar. 11, 2013

(86) PCT No.: PCT/EP2013/054851
§ 371 (c)(1),
(2) Date: Sep. 22, 2014

(87) PCT Pub. No.: WO2013/149791
PCT Pub. Date: Oct. 10, 2013

(65) Prior Publication Data
US 2015/0037267 A1 Feb. 5, 2015

(30) Foreign Application Priority Data

Apr. 3, 2012 (IN) .................. 1092/MUM/2012
Jul. 12, 2012 (EP) ...................... 12176126

(51) Int. Cl.
| A61K 36/48 | (2006.01) |
| A61K 8/97 | (2017.01) |
| A61K 8/60 | (2006.01) |
| A61Q 19/02 | (2006.01) |
| A61Q 1/00 | (2006.01) |
| A61Q 5/02 | (2006.01) |
| A61Q 5/12 | (2006.01) |
| A61Q 9/04 | (2006.01) |
| A61Q 15/00 | (2006.01) |
| A61Q 17/04 | (2006.01) |
| A61Q 19/00 | (2006.01) |
| A61Q 19/04 | (2006.01) |
| A61Q 19/10 | (2006.01) |

(52) U.S. Cl.
CPC .............. *A61K 8/97* (2013.01); *A61K 8/602* (2013.01); *A61Q 1/00* (2013.01); *A61Q 5/02* (2013.01); *A61Q 5/12* (2013.01); *A61Q 9/04* (2013.01); *A61Q 15/00* (2013.01); *A61Q 17/04* (2013.01); *A61Q 19/007* (2013.01); *A61Q 19/02* (2013.01); *A61Q 19/04* (2013.01); *A61Q 19/10* (2013.01); *A61K 2800/30* (2013.01); *A61K 2800/782* (2013.01)

(58) Field of Classification Search
CPC ...................................................... A61K 36/48
See application file for complete search history.

(56) References Cited

U.S. PATENT DOCUMENTS

| 7,189,419 | B2 | 3/2007 | Mahalingam et al. | |
| 7,815,933 | B2 * | 10/2010 | Holmberg ............ | A61K 9/1075 |
| | | | | 424/450 |
| 8,058,051 | B2 * | 11/2011 | Nose .................. | A23L 2/52 |
| | | | | 424/93.4 |
| 2004/0115146 | A1 | 6/2004 | Mahalingam | |
| 2006/0280817 | A1 | 12/2006 | Saxena et al. | |
| 2008/0206373 | A1 | 8/2008 | Millikin | |
| 2009/0221690 | A1 * | 9/2009 | Maurya .................. | A61K 31/35 |
| | | | | 514/453 |
| 2010/0221369 | A1 * | 9/2010 | Mitra ..................... | A61K 8/97 |
| | | | | 424/757 |
| 2011/0052517 | A1 | 3/2011 | Santhanam | |
| 2015/0140141 | A1 * | 5/2015 | Milow .................. | A61K 36/18 |
| | | | | 424/757 |

FOREIGN PATENT DOCUMENTS

| CN | 1694716 | | 11/2006 |
| CN | 101287481 | | 10/2008 |
| CN | 101474194 A | * | 7/2009 |
| CN | 101621987 | | 1/2010 |
| WO | WO 2006/111251 A | * | 10/2006 |
| WO | WO2006126067 | | 11/2006 |
| WO | WO2008151890 | | 12/2008 |
| WO | WO2008151891 | | 12/2008 |

OTHER PUBLICATIONS

Michel et al. Separation and Purification Technology. 2011. vol. 80, pp. 32-37.*
IPRP in PCTEP2013054851 dated Mar. 11, 2013.
IPRP2 in PCTEP2013054851 dated Jul. 10, 2014.
Gupta et al., "The Glucosides of Butea Monosperm", Phytochemistry, vol. 9, pp. 2231 to 2235.
Search Report in EP12176126 dated Dec. 18, 2012.
Search Report in PCTEP2013054851 dated Jul. 3, 2013.
Wagner et al., "Isobutrin and Butrin, the Antihepatotoxic Principles of Butea monosperma Flowers", Planta Medica, Jan. 1985, No. 2, pp. 77-79 (XP008068784).
Written Opinion in EP12176126 dated Dec. 18, 2012.
Written Opinion in PCTEP2013054851 dated Jul. 3, 2013.

* cited by examiner

*Primary Examiner* — Chris R Tate
(74) *Attorney, Agent, or Firm* — Greenberg Traurig, LLP

(57) ABSTRACT

The present invention relates to a personal care composition for topical application having skin lightening application. It is an object of the present invention to provide for a personal care composition that comprises fractions obtained from natural sources that gives enhanced skin lightening as compared to known fractions from natural sources.

4 Claims, No Drawings

PERSONAL CARE COMPOSITION

FIELD OF THE INVENTION

The present invention relates to a personal care composition for topical application comprising selective fractions of natural materials having skin lightening efficacy.

BACKGROUND OF THE INVENTION

Highly pleasing skin appearance is one of the most desired expectations from personal care products from most consumers around the world. In tropical countries where consumers generally have dark skin, there is a desire to have lighter skin appearance. In consumers who live far from the tropical countries e.g. the Caucasian people who generally have lighter skin, there is a need among such consumers to have an even tanned tone of their skin. Any exposure of the skin to sunlight, in such consumers often leads to blotchy skin, referred to as freckles and in some cases they experience hyperpigmentation in localized areas of the skin. Most consumers experience blemishes on their skin after exposure to sun, on healing of wounds or after drying up of acne. Most people, all over the world, notice darker skin on their underarms (i.e in their axilia) as compared to other regions of their skin, although the underarms are rarely exposed to the sun. They prefer an even skin tone in their axilia as compared to other parts of the body. In all of the above cases, consumers rely on cosmetic solutions to their skin appearance problems.

Thus, smooth, soft and glowing skin with even skin tone and colour is desired by all consumers who use personal care compositions for their skin. To provide this benefit, one very commonly used approach is to include sunscreens or sunblocks in such cosmetic products. Another approach to controlling the colour, tone and appearance of the skin is the skin lightening approach where chemicals are added to personal care compositions which alter the formation of melanin in the skin through biochemical transformation in the stratum corneum thereby changing the colour and appearance of the skin. This approach is capable of lightening the skin beyond the basic colour of skin. While this approach has been used successfully in many cosmetic products, researchers are still struggling to improve efficacy of skin lightening agents beyond a certain threshold.

One of the drawbacks of most skin lightening actives used so far is that they are usually synthetically prepared chemical compounds. Synthetic chemicals have over time, taken a negative connotation in the consumer's mind. Hence, many consumers are more and more, preferring actives originating from or extracted from natural sources to be used in such products.

In order to provide a solution to the several drawbacks in the art listed above, the present inventors have been working for many years on deriving actives from natural sources for various personal care benefits. They found to their surprise that fractions of plant material, enriched in butrin beyond a certain minimum percentage exhibit skin lightening activity.

JP 10101543A (Kansai Koso, 1998) discloses a tyrosinase-activity inhibitor that contains, as its effective ingredient, 0.0001 weight percent or more of a flavonoid having OH at sites 2 and 4 such as a chalcone derivative of formula I (R1-R7 are each H or OH, where at least one of sites 2 and 4, or sites 2' and 4' is OH, a flavanone of formula II (R8-R10 are each H or OH), a flavone derivative of formula III (R11-R13 are H or OH), or a mixture of them, thereby enabling strong inhibition of tyrosinase activity related to melanin formation.

US 2004115146A (Avon Products) discloses a composition having at least one of the following active extracts *Butea frondosa, Naringi crenulata, Stenoloma chusana*, or any combinations thereof. There is also provided a composition having at least one of the following additional extracts *Azadirachta indica, Glycyrrhiza glabra linn., Morinda citrifolia, tomato glycolipid* or any combinations thereof in combination with one or more of the active extracts. The compositions and methods of the invention are effective to lighten hair, skin, lips and/or nails.

The above publications do not disclose a skin lightening composition comprising a plant extract comprising higher than 15% butrin.

It is thus an object of the present invention to provide for a personal care composition that comprises fractions obtained from natural sources that gives enhanced skin lightening as compared to known fractions from natural sources.

SUMMARY OF THE INVENTION

According to the first aspect of the invention there is provided a personal care composition comprising
(a) 0.01 to 10% by weight of an extract of a plant source which comprises higher than 15% butrin by weight of the extract; and
(b) a cosmetically acceptable base selected from an emulsion, lotion, cream, foam, gel, soap bar, stick, mask, pad or patch.

According to a preferred aspect of the invention, the plant source is *Butea monosperma*.

According to another preferred aspect of the present invention the extract of Butea monosperma for use in the composition of the invention is prepared using a process comprising the steps of
(a) heating the plant source in water at a temperature in the range of 30 to 80° C.,
(b) separating the insoluble matter to prepare an aqueous fraction;
(c) precipitating the extract by adding a mixture of methanol and ethanol to said aqueous fraction; and
(d) separating said extract from the mixture of step (c).

According to yet another aspect of the invention there is provided use of an extract of a plant source *Butea monosperma* which comprises higher than 15% butrin by weight of the extract as a skin lightening agent.

DETAILED DESCRIPTION OF THE INVENTION

These and other aspects, features and advantages will become apparent to those of ordinary skill in the art from a reading of the following detailed description and the appended claims. For the avoidance of doubt, any feature of one aspect of the present invention may be utilized in any other aspect of the invention. The word "comprising" is intended to mean "including" but not necessarily "consisting of" or "composed of." In other words, the listed steps or options need not be exhaustive. It is noted that the examples given in the description below are intended to clarify the invention and are not intended to limit the invention to those examples per se. Similarly, all percentages are weight/weight percentages unless otherwise indicated. Except in the operating and comparative examples, or where otherwise explicitly indicated, all numbers in this description indicating amounts of material or conditions of reaction, physical properties of materials and/or use are to be understood as modified by the word "about". Numerical ranges expressed in the format "from x to y" are understood to include x and y. When for a specific feature multiple preferred ranges are described in the format "from x to y", it is understood that all ranges combining the different endpoints are also contemplated.

"Personal Care Composition" as used herein, is meant to include a composition for topical application to skin of mammals, especially humans. Such a composition may be generally classified as leave-on or rinse off, and includes any product applied to a human body for improving appearance, cleansing, odor control or general aesthetics. The personal care composition is preferably a leave-on composition. The composition of the present invention can be in the form of a liquid, lotion, cream, foam, scrub, gel, soap bar or toner, or applied with an implement or via a face mask, pad or patch. Non-limiting examples of personal care compositions include leave-on skin lotions and creams, shampoos, conditioners, shower gels, toilet bars, antiperspirants, deodorants, depilatories, lipsticks, foundations, mascara, sunless tanners and sunscreen lotions. Thus the preferred cosmetically acceptable base is an emulsion, lotion, cream, foam, gel, soap bar, stick, mask, pad or patch. Preferred cosmetically acceptable base in leave-on compositions are an emulsion, lotion, cream, foam, gel or stick. "Skin" as used herein is meant to include skin on the face and body (e.g., neck, chest, back, arms, underarms, hands, legs, buttocks and scalp).

The invention provides for a personal care composition for providing skin lightening benefits comprising an extract of a plant source, the extract comprising more than 15% butrin by weight of the extract, on dry weight basis. The extract is present in 0.01 to 10%, preferably 0.1 to 5%, more preferably 0.1 to 2.5% by weight of the composition. Butrin is preferably present in higher than 20%, more preferably higher than 30%, further more preferably higher than 35% by dry weight basis of the extract of the plant source. Butrin is preferably present in from 0.0001 to 2%, more preferably 0.001 to 1% by weight of the composition.

The chemical structure of butrin is given below

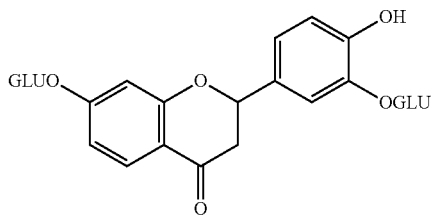

where GLU refers to a glucose unit. The plant source that is preferably used for extracting the enriched fraction of butrin is *Butea monosperma*. Aqueous extracts of *Butea monosperma* usually contain from 8 to 12% butrin. Thus butrin, for use in the personal care composition of the invention, is preferably sourced from enriched fractions of *Butea monosperma*.

*Butea monosperma* is a species of Butea native to tropical and sub-tropical parts of the Indian Subcontinent and South-east Asia. Common names include Palash, Dhak, Palah, Flame of the Forest, and Bastard Teak.

It is a medium sized dry season-deciduous tree, growing to about 15 m high. It is a slow growing tree. It is used for timber, resin, fodder, medicine, and dye. The gum from the tree is used in certain food dishes. The gum is also known as Bengal Kino and is considered valuable by druggists because of its astringent qualities and by leather workers because of its tannin.

The constituents of aqueous extract of the flower of *Butea monosperma* are dihydromonospermoside, butein, monospermoside, isoliquiritigenin, 7,3',4'-trihydroxyflavone, four flavanones, butin, butrin, isomonospermoside. liquiritigenin, formononetin, afrormosin and formononetin-7-O-beta-D-glucopyranoside.

The extract of plant source for use in the composition of the invention preferably comprises less than 2% isobutein by weight of the extract, more preferably less then 1% by weight of the extract. Isobutein has the chemical structure:

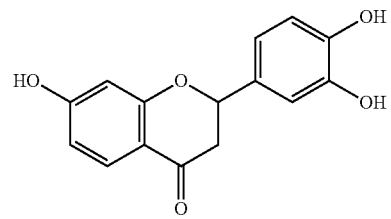 [SMILES: O=C1CC(c2ccc(O)c(O)c2)Oc2cc(O)ccc21]

The extract of plant source for use in the composition of the invention preferably comprises less than 2% butein by weight of the extract, more preferably less then 1% by weight of the extract. Butein has the chemical structure:

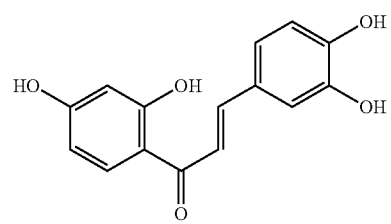 [SMILES: O=C(/C=C/c1ccc(O)c(O)c1)c1ccc(O)cc1O]

The personal care composition comprises a cosmetically acceptable base. The cosmetically acceptable base is preferably a cream, lotion, gel or emulsion.

Personal care compositions may be prepared using different cosmetically acceptable emulsifying or non-emulsifying systems and vehicles. Preferred cosmetically acceptable bases comprise 1 to 25% fatty acid, by weight of the composition. A further preferred aspect provides for inclusion of 0.1 to 10% soap by weight of the composition. A highly suitable base is a cream. Vanishing creams are especially preferred. Vanishing cream bases generally comprise 5 to 25% w/w fatty acid and 0.1 to 10% w/w soap. Vanishing cream base gives a highly appreciated matty feel to the skin. $C_{12}$ to $C_{20}$ fatty acids are especially preferred in vanishing cream bases, further more preferred being $C_{14}$ to $C_{18}$ fatty acids. The most preferred fatty acid is stearic acid. The fatty acid may also be a mixture of palmitic and stearic acid. The fatty acid in the composition is more preferably present in an amount in the range of 5 to 20% w/w of the composition. Soaps in the vanishing cream base include alkali metal salt of fatty acids, like sodium or potassium salts, most preferred being potassium stearate. The soap in the vanishing cream base is generally present in an amount in the range of 0.1 to 10%, more preferably 0.1 to 3% w/w of the composition. Generally the vanishing cream base in cosmetic compositions is prepared by taking a desired amount of total fatty matter and mixing with potassium hydroxide in desired amounts. The soap is usually formed in-situ during the mixing. The personal care composition when formulated as a vanishing cream preferably comprises 60 to 85%, more preferably 65 to 80% w/w water.

The composition of the invention may comprise another skin lightening agent other than the extract of the invention. This additional skin lightening agent is preferably chosen from a vitamin B3 compound or its derivative e.g. niacin, nicotinic acid, niacinamide or any other well known skin lightening agent. Most preferred additional skin lightening agent is niacinamide. Niacinamide, when used, is preferably present in an amount in the range of 0.1 to 10%, more preferably 0.2 to 5% w/w of the composition.

The personal care composition may preferably additionally comprise one or more UV sunscreens. The UV sunscreens may be inorganic or organic. A wide variety of organic sunscreen agents are suitable for use in combination with the essential ingredients of this invention. Most suitable organic sunscreen are 2-ethylhexyl-p-methoxycinnamate (as a UVB sunscreen agent) and/or butylmethoxydibenzoylmethane (as a UVA sunscreen agent).

A safe and effective amount of sunscreen may be used in the compositions of the present invention. The composition preferably comprises from about 0.1% to about 10%, more preferably from about 0.1% to about 5% w/w of a sunscreen agent.

Useful inorganic sun-blocks are also preferably used in the present invention. These include, for example, zinc oxide iron oxide, silica, such as fumed silica, and titanium dioxide.

Ultrafine titanium dioxide in either of its two forms, namely water-dispersible titanium dioxide and oil-dispersible titanium dioxide is especially suitable for the invention. Water-dispersible titanium dioxide is ultra-fine titanium dioxide, the particles of which are non-coated or which are coated with a material to impart a hydrophilic surface property to the particles. Examples of such materials include aluminium oxide and aluminium silicate.

Oil-dispersible titanium dioxide is ultrafine titanium dioxide, the particles of which exhibit a hydrophobic surface property, and which, for this purpose, can be coated with metal soaps such as aluminium stearate, aluminium laurate or zinc stearate, or with organosilicone compounds.

By "ultrafine titanium dioxide" is meant particles of titanium dioxide having an average particle size of less than 100 nm, preferably 70 nm or less, more preferably from 10 to 40 nm and most preferably from 15 to 25 nm. The total amount of sun block that is preferably incorporated in the composition according to the invention is from 0.1 to 5% w/w of the composition.

The composition according to the invention may also comprise other diluents. The diluents act as a dispersant or carrier for other materials present in the composition, so as to facilitate their distribution when the composition is applied to the skin.

Diluents other than water can include liquid or solid emollients, solvents, humectants, thickeners and powders.

The cosmetically acceptable base is usually from 10 to 99.9%, preferably from 50 to 99% w/w of the composition, and can, in the absence of other cosmetic adjuncts, form the balance of the composition. The composition of the invention may comprise water.

The composition of the invention may comprise a conventional deodorant base as the cosmetically acceptable carrier. By a deodorant is meant a product in the stick, roll-on, or propellant medium which is used for personal deodorant benefit e.g. application in the under-arm area which may or may not contain anti-perspirant actives.

Deodorant compositions can generally be in the form of firm solids, soft solids, gels, creams, and liquids and are dispensed using applicators appropriate to the physical characteristics of the composition.

Deodorant compositions which are delivered through roll-ons generally comprise a liquid carrier. Such liquid carrier can be hydrophobic or comprise a mixture of both hydrophilic and hydrophobic liquids. They may be in the form of an emulsion or a microemulsion. The liquid carrier or mixture of carriers often constitutes from 30 to 95% and in many instances from 40 to 80% w/w of the composition.

Hydrophobic liquid carriers commonly can comprise one or more materials selected within the chemical classes of siloxanes, hydrocarbons, branched aliphatic alcohols, esters and ethers that have a melting point not higher than 25° C. and a boiling point of at least 100° C.

Hydrophilic carrier liquids that can be employed in compositions herein commonly comprise water and/or a mono or polyhydric alcohol or water-miscible homologue. Monohydric alcohols often are short chain, by which is meant that they contain up to 6 carbons, and in practice are most often ethanol or sometimes iso-propanol. Polyhydric alcohols commonly comprise ethylene or propylene glycol, or a homologue can be employed such as diethylene glycol.

The compositions that remain in liquid form can be applied employing conventional applicators such as a roll-on or by being pumped or squeezed through a spray-generating orifice. Such compositions may be thickened, for example using one or more thickeners described subsequently herein.

Compositions that are firm solids, commonly obtained by use of a gellant or structurant, can be applied employing a stick applicator and soft solids, gels and creams can be applied employing an applicator having a dispensing head provided with at least one aperture through which the soft solid, gel or cream can be extruded under mild pressure.

Suitable thickeners or gellants that may be used for achieving this is by use of water-soluble or dispersible materials of higher viscosity, including various of the emulsifiers, and/or thickened or gelled with water-soluble or water-dispersible polymers including polyacrylates, and water-soluble or dispersible natural polymers, such as water-soluble polysaccharide or starch derivatives, such as alginates, carageenan, agarose and water-dispersible polymers include cellulose derivatives.

The concentration of such polymers in the water-immiscible liquid is often selected in the range of from 1 to 20% w/w depending on the extent of thickening or structuring required, and the effectiveness of the chosen polymer in the liquid/mixture.

One class of structurant which is desirable by virtue of its long standing proven capability to produce firm solids and more recently in making soft solids, comprises waxes. Herein, the term wax is employed to encompass not only materials of natural origin that are solid with a waxy feel and water-insoluble at 30-40° C., but melt at a somewhat higher temperature, typically between 50 and 95° C., such as beeswax, candelilla or carnauba wax, but also materials having similar properties. Such other waxes include hydrocarbon waxes, eg paraffin wax, mineral wax and microcrystalline wax; synthetic waxes, such as polyethylene of 2000 to 10000 daltons; waxy derivatives or waxy components of natural waxes Mixtures of materials within each class of gellant/structurant can be employed.

When a deodorant composition employed herein comprises an aerosol composition, it contains a propellant in addition to a base composition as described herein above, commonly in a weight ratio of from 95:5 to 40:60, and in many formulations, the weight ratio is from 90:10 to 50:50.

The propellant is conveniently a low boiling point material, typically boiling below −5° C., for example an alkane such as propane, butane or isobutane, and possibly containing a fraction of pentane or isopentane, or a hydrofluorocarbon or fluorocarbon of similar carbon content. During filling of the aerosol canister, the propellant gas is liquified by virtue of the elevated pressure that is generated therein.

The compositions of the present invention can comprise a wide range of other optional components. The CTFA Cosmetic Ingredient Handbook, Second Edition, 1992, which is incorporated by reference herein in its entirety, describes a wide variety of non-limiting cosmetic and pharmaceutical ingredients commonly used in the skin care industry, which are suitable for use in the compositions of the present invention. Examples include: antioxidants, binders, biological additives, buffering agents, colorants, thickeners, polymers, astringents, fragrance, humectants, opacifying agents, conditioners, exfoliating agents, pH adjusters, preservatives, natural extracts, essential oils, skin sensates, skin soothing agents, and skin healing agents.

The composition is formulated in any known format, more preferred formats being creams or lotions.

Process

The invention also provides for a composition where the plant extract is prepared using a process comprising the steps of
(a) heating the plant source in water at a temperature in the range of 30 to 80 ° C.,
(b) separating the insoluble matter to prepare an aqueous fraction;
(c) precipitating the extract by adding a mixture of methanol and ethanol to said aqueous fraction; and
(d) separating said extract from the mixture of step (c).

According to a preferred aspect the mixture of methanol and ethanol is in the weight ratio of 80:20 to 95:5 methanol:ethanol.

According to yet another aspect of the invention the plant extract is prepared using a process comprising the steps of
(a) extracting the plant source with water; followed by
(b) sequential extraction with higher polarity solvents selected from diethyl ether, ethyl acetate and butanol.

According to a further preferred aspect the extraction is first carried out with water, followed by diethyl ether, followed by ethyl acetate and finally with butanol.

According to another aspect of the present invention there is provided a method of lightening skin comprising the step of applying a composition of the invention on the desired skin surface.

According to yet another aspect of the invention there is provided use of an extract of a plant source Butea monosperma which comprises higher than 15% butrin by weight of the extract as a skin lightening agent.

According to yet another aspect of the invention there is provided an extract of a plant source Butea monosperma which comprises higher then 15% butrin for use in skin lightening.

The use is preferably non-therapeutic.

The Butea monosperma for use in the present invention was purchased from Shroff Channabasappa & Sons, Bangalore India who sourced it from India.

The invention is now further described by way of the following non-limiting examples.

EXAMPLES

Example 1 to 4: Tyrosinase inhibition obtained using extracts of plant material in comparison with known actives:

Example 1

Aqueous Extract 100 grams of dried flowers of Butea monosperma were extracted with 800 ml water at 25° C. at 800 mb vacuum. The liquor containing the extract was dried to obtain about 25 gram of dried extract. The dried extract was found to contain about 9.8% butrin.

Example 2

Extraction with Sequential Polarity Solvents

The extract from Example-1 was sequentially extracted first with diethyl ether, then with ethyl acetate and finally with butanol to obtain about 2.8 gm of dried extract which was found to contain 41.1% butrin.

Example 3

Kojic Acid was used as a Positive Control

The samples at various concentrations were analysed for skin lightening efficacy using the coculture melanin content assay, the details of which are given below:
Set up of Co-cultures:
1. $4*10^4$ HaCaT and $4×10^4$ HeMnDP (1:1) per well (single wells/treatment) in 12-well Nunc plates on Day 0 are seeded so as to establish a co-culture system.
2. The volume of media per well should be 1 mL of a 1:1 mix of Melanocyte Growth Media and Keratinocyte Growth Media
3. 24 hrs later, fresh media containing actives are added. Again 1 mL of a 1:1 mix of MGM and KGM for active addition are used.
4. Plates are incubated for 72 hrs in a 37° C. $CO_2$ incubator.
5. At the end of the time point, the plates are progressed for Calcein assay followed by melanin content estimation.
Calcein-AM Viability Assay
1. The spent media are removed from all wells of a 12 well plate and rinsed once with 400 µl of 1×PBS—Ca—Mg (see preparation below), including wells without cells (control wells).
2. 1 µM of Calcein-AM (working stock) in 1×PBS—Ca—Mg from 1 mM stock (e.g. 10 ul of 1 mM Calcein stock in 100% DMSO in 10 ml of 1×PBS—Ca—Mg) is prepared. 400 µl of above Calcein-AM working stock solution is added to each well including controls cells.
3. The plates are covered with aluminum foil completely and incubated for 30 minutes in the regular $CO_2$ incubator.
4. In the meantime, the fluorescence is measured (excitation at 490 nm and emission at 520 nm) using TECAN instrument after 30 min of dye incubation.
5. After reading the plate, the buffer containing Calcein is removed and melanin content assay is then carried out.
Preparation of PBS—Ca—Mg
20×PBS—Ca—Mg stock buffers (for 1 liter solution)

Solution A:
348 mM Na2HPO4 (anhydrous) . . . 49.4 g
70 mM NaH2PO4 (dihydrate) . . . 10.92 g
Solution B:
18 mM CaCl2 . . . 2.6 g
70 mM KCl . . . 5.22 g
18 mM MgCl2 (hexahydrate) . . . 3.66 g
2740 mM NaCl . . . 160.3 g 50 ml of each of Solutions A and B are prepared in autoclaved distilled water and stored at room temperature (storing at 4° C. can lead to precipitation).

1×PBS—Ca—Mg working stock 5 ml each of solutions A and B are taken and 90 ml of water is added to it, to make the working stock. It is filtered just before use.

Preparation of 1 mM Calcein-AM stock 1. 500 µl of 100% DMSO is added to 1 mg of Calcein AM (Fluka/Sigma Aldrich, CAS No 148504-34-1).
2. It is well mixed and another 500 µl of 100% DMSO is added to it.
3. It is then well mixed, taken in 20 µl aliquot covered with Al foil and stored at −20° C.

Melanin Content Assay

Preparation of MCA reagent (10% DMSO in 1N NaOH)

| Volume of MCA reagent (mL) | Volume of DMSO (100%) (mL) | Volume of 10N NaOH (mL) | Volume of water (mL) |
|---|---|---|---|
| 10 | 1 | 1 | 8 |

1. After the reading for Calcein-AM is taken, the buffer containing Calcein-AM is removed from all the wells.
2. 150 µl of above MCA reagent is added to each well.
3. The plates are incubated for 1 hr at 60° C. with gentle shaking.
4. 120 µl of solution is transferred from each well into a 384 well plate.
5. The absorbance is measured in the Lab-5 Tecan instrument at 405 nm.
6. For non-cytotoxic concentrations (based on Calcein cut-off of ±15% of control), the average MCA is calculated and reported as MCA as percentage of the control sample. The % inhibition is then calculated.

Thus the higher the value of % inhibition, the more the active has potential as a skin lightening agent.

The data on the % inhibition is summarized in Table 1

TABLE 1

| Sample | Concentration | % Inhibition |
|---|---|---|
| Example 1 | 10 ppm | 27 |
| Example 2 | 5 ppm | 47 |
| Example 3 | 14.2 ppm | 22 |

The data in Table 1 indicates that a sample as per the invention (Example 2) provided for vastly improved skin lightening efficiency as compared to the aqueous extract of the same plant material (Example 1). Further Example 2 is vastly superior to other known active Kojic acid (Example 3) at even lower concentration.

Examples 4 and 5: Efficacy of Pure Butrin Obtained from Plant Material in Comparison to a Control Example 4

Pure Butrin from Plant Material

The dried extract of Example 1 was taken in a methanol:ethanol (90:10) mixture and sonicated for 20 minutes. The mixture was then allowed to cool at about 10° C. for about a one day. The precipitate obtained was then collected and dried to a powder. This contained about 90% butrin. This samples was then further purified by crystallization with methanol followed by dichloromethane to get pure butrin.

Example 5

Kojic Acid

The samples at various concentrations were analysed for skin lightening efficacy using the co-culture melanin content assay.

The data on the % inhibition is summarized in Table 2.

TABLE 2

| Molecule | Concentration | % Inhibition |
|---|---|---|
| Butrin | 0.5 ppm | 31 |
| Kojic acid | 14.2 ppm | 22 |

The data in Table 2 indicates that pure butrin obtained from plant material also provides for excellent skin lightening efficacy.

The invention claimed is:

1. A personal care composition comprising
   an extract of *Butea monosperma*, wherein the extract comprises
   butrin,
      wherein an amount of butrin is higher than 20% by dry weight of the extract;
   isobutein,
      wherein an amount of isobutein is less than 2% by dry weight of the extract,
   butein,
      wherein an amount of butein is less than 2% by dry weight of the extract; and
   a cosmetically acceptable base selected from an emulsion, lotion, cream, foam, gel, bar of soap, stick, mask, pad or patch;
   wherein the personal care composition is selected from leave-on skin lotions and creams, shampoos, conditioners, shower gels, toilet bars, antiperspirants, deodorants, depilatories, lipsticks, foundations, mascara, sunless tanners and sunscreen lotions.

2. A composition as claimed in claim 1, wherein said cosmetically acceptable base further comprises 1 to 25% fatty acid.

3. A composition as claimed in claim 1, wherein said cosmetically acceptable base further comprises 0.1 to 10% soap.

4. A method of lightening skin of a subject in need thereof comprising the step of applying an effective amount of the composition as claimed in claim 1 for a sufficient duration of time to the skin of the subject to achieve the lightening of the skin.

* * * * *